US007071211B2

(12) United States Patent
Pfeffer et al.

(10) Patent No.: US 7,071,211 B2
(45) Date of Patent: Jul. 4, 2006

(54) SMALL ORGANIC MOLECULES THAT INCREASE THE ACTIVITY OF GELATINASE A IN OCULAR CELLS

(75) Inventors: Bruce Alan Pfeffer, Fairport, NY (US); Rosemarie Beth Flick, Copiaque, NY (US); Naveed Bin Kamal Shams, Duluth, GA (US); Stephen Paul Bartels, Pittsford, NY (US)

(73) Assignee: Bausch & Lomb Inc., Rochester, NY (US)

( * ) Notice: Subject to any disclaimer, the term of this patent is extended or adjusted under 35 U.S.C. 154(b) by 183 days.

(21) Appl. No.: 10/260,448

(22) Filed: Sep. 27, 2002

(65) Prior Publication Data

US 2004/0068017 A1 Apr. 8, 2004

(51) Int. Cl.
*A61K 31/445* (2006.01)
*A61K 31/44* (2006.01)
*C09D 211/02* (2006.01)
*C09D 207/02* (2006.01)

(52) U.S. Cl. .................. 514/315; 514/354; 546/184; 548/530; 548/531

(58) Field of Classification Search ............. 546/184; 548/530, 531; 514/315, 354
See application file for complete search history.

(56) References Cited

U.S. PATENT DOCUMENTS

| 3,290,320 | A | 12/1966 | Villani ..................... 260/295 |
| 3,686,409 | A | 8/1972 | Plotnikoff ................. 424/272 |
| 3,975,533 | A | 8/1976 | Kodama et al. ........... 424/326 |
| 4,347,372 | A | 8/1982 | Fory et al. ................ 548/217 |
| 4,453,974 | A | 6/1984 | Martin ...................... 71/105 |
| 5,260,059 | A | 11/1993 | Acott et al. ............. 424/94.67 |
| 5,438,056 | A | 8/1995 | Felman et al. .......... 514/224.5 |
| 5,668,133 | A | * | 9/1997 | Yanni et al. ............... 514/218 |
| 6,566,384 | B1 | * | 5/2003 | Owen et al. ............... 514/390 |

FOREIGN PATENT DOCUMENTS

| DE | 2403100 | * | 8/1974 |
| DE | 2639969 | * | 3/1977 |
| EP | 0035945 | A | | 9/1981 |
| EP | 0118078 | * | 9/1984 |
| FR | 1455835 | A | | 5/1966 |
| GB | 1365847 | A | | 9/1974 |

OTHER PUBLICATIONS

"Mechanisms of Action of Carbamazepine and Its Derivatives, Oxcarbazepine, BIA 2–093, and BIA 2–024", by Ambrosio et al., *Neurochemical Research*, vol. 27, Nos. 1/2, 2/02.
Database Crossfire Beilstein, Registry No. 6881299, Beilstein Institut zur Foerderung der Chemischen Wissenschaften, vol. 38, No. 4, 1983, pp. 255–264.
"The Activation, Expression and Function of Gelatinase A (MMP–2)", Hewitt et al., *Trends in Glycoscience and Glycotechnology*, vol. 8, No. 39, 1/96, pp. 23–36.
"Protein Tyrosine Phosphorylation in Signalling Pathways Leading to the Activation of Gelatinase A: Activation of Gelatinase A by Treatment with the Protein Tyrosine Phosphatase Inhibitor Sodium Orthovanadate", Li et al., *Biochimica et Biophysica Acta* 1405, 1998, pp. 110–120.
The FASEB Journal (vol. 12), Article: Matrix metalloproteinases: structures, evolution, and diversification, Authors: Irinia Massova, Lakshmi P. Kotra, Rafael Eridman, and Shahriar Mobashery, Date: Sep. 1998, pp. 1075–1095.
Medical Microbiology and Immunology (182), Article: A guide to the use of pore–forming toxins for controller permeabilization of cell membranes, Authors: Sucharit Bhakdi, Ulrich Weller, Iwan Walev, Edith Martin, Daniel Jonas, and Michael Palmer, Date: 1993, pp.: 167–175.
Biochem J. (307), Article: The translocation, folding, assembly and redox–dependent degradation of secrtory and membrane proteins in semi–permeabilized manmmalian cells, Authors: Richard Wilson, Amanda J. Allen, Jason Oliver, Jayne L. Brookman, Stephen High, and Neil J. Bulleid, Date: 1995, pp.: 679–687.
The Journal of Cell Biology (vol. 119, No. 5), Article: Morephological Analysis of Protein Transport from the ER to Golgi Membranes in Digitonin–permeabilized Cells: Role of the P58 Containing Compartment, Authors: Helen Plutner, Howard W. Davidson, Jaakko Saraste, and William E. Balch, Date: Dec. 1992, pp.: 1097–1116.
Cytometry (17), Article: Reliable Method for the Simultaneous Detection of Cytoplasmic and Surface CD3 Expression by Murine Lymphoid Cells, Authors: Karl J. Franek, R. Michael Wolcott, and Robert Chervenak, Date: 1994, pp.: 224–236.
The Journal of Nueroscience (16), Article: Distinct Properties of Neuronal and Astrocytic Endopeptidase 3.4.24.16: A Study on Differentiation, Subcellular Distribution, and Secretion Processes, Authors: Bruno Vincent, Alain Beaudet, Pascale Dauch, Jean–Pierre Vincent, and Frederic Checler, Date: Aug. 15, 1996, pp.: 5049–5059.
Article: Expression of Membrane Type Matrix Metalloproteinase (MT–MMP) and Activation of MMP–2 in Lung Cancer, Authors: Masato Tokuraku, Hiroshi Sato, Yoh Watanube, Motoharu Seiki, Date: 1996, pp.: 266–270.
Ophthalmology (vol. 90, No. 7), Article: Why Is Intraocular Pressure Elevated in Chronic Simple Glaucoma, Author: Johannes W. Rohen, M.D., Date: Jul. 1983, pp.: 758–765.

(Continued)

*Primary Examiner*—Rita Desai
(74) *Attorney, Agent, or Firm*—Paul Lavoie

(57) ABSTRACT

Small organic molecules capable of effecting a "pharmacological trabeculocanalotomy" in an eye by means of reducing juxtacanalicular meshwork as a barrier to outflow of aqueous. The small organic molecules increase Gelatinase A activity in ocular cells by increasing cell membrane expression of membrane-type matrix metalloproteinases (MT-MMPs) to increase aqueous outflow as a treatment for primary open angle glaucoma.

10 Claims, No Drawings

OTHER PUBLICATIONS

ACTA Ophthalmologica (vol. 50), Article: Scanning Electron Microscopic Studies of the Trabecular Meshwork and the Canal of Schlemm an Attempt to Localize the Main Resistance to Outflow of Acueous Humor in Man, Authors: Bill Anders and Svedbergh Bjorn, Date: 1972, pp.: 295–320.

Investigative Ophthalmology & Visual Science (vol. 30, No. 9), Article: Proteins Secreted by Human Trabecular Cells, Authors: Andersen, J. Yun, Collin G. Murphy, Jon R. Polansky, David A. Newsome, and Jorge A. Alvarado, Date: Sep. 1989, pp.: 2012–2022.

In Vitro Cellular & Developmental Biology (vol. 23, No. 7), Article: Optimized Medium for Clonal Growth of Human Microvascular Endothelial Cells with Minimal Serum, Authors: Ann Knedler and Richard G. Ham, Date: Jul. 1987, pp.: 481–491.

Gerontologie (26), Article: Stimulatory effects of ascorbic acid on hyaluronic acid synthesis of in vitro cultured normal and glaucomatous trabecular meshwork cells of the human eye, Authors: D. O. Schachtschabel and E. Binninger, Date: 1993, pp.: 243–246.

Current Eye Research (vol. 11, No. 11), Article: Proteolytic activation of corneal matrix metalloproteinase by Pseudomonas aeruginosa, Authros: Koki Matsumoto, Naveed B. K. Sbams, Laila A. Hanninen and Kenneth R. Kenyon, Date: 1992, pp.: 1105–1109.

* cited by examiner

SMALL ORGANIC MOLECULES THAT INCREASE THE ACTIVITY OF GELATINASE A IN OCULAR CELLS

FIELD OF THE INVENTION

The present invention relates generally to small organic molecules capable of effecting a "pharmacologic trabeculocanalotomy" in an eye by means of reducing juxtacanalicular meshwork as a barrier to outflow of aqueous. More specifically, the present invention relates to small organic molecules that increase Gelatinase A activity in ocular cells by increasing cell membrane expression of membrane-type matrix metalloproteinases (MT-MMPs) to increase aqueous outflow as a treatment for primary open angle glaucoma. The present invention likewise includes methods of manufacturing and using such small organic molecules in the treatment of primary open angle glaucoma.

BACKGROUND OF THE INVENTION

The extracellular matrix (ECM) of an eye is an association of specialized proteins, glycoproteins, and proteoglycans, that subserve and impart structure to the physiological functions of connective tissues. At the cellular level, the ECM not only provides structure, flexibility and support, but also acts as a filtration barrier, mediates cell attachment and influences tissue morphogenesis and differentiation. Part of the normal functioning of the ECM involves the ECM's tightly regulated turnover, which balances the degradation and disposal of effete molecules with the secretion and integration of the various newly synthesized ECM elements.

Specialized extracellular proteolytic enzymes, termed matrix metalloproteinases (MMPs), are produced by many cell types. MMPs play an important role in the initial degradation of such ECM molecules as collagen, fibronectin and various proteoglycans. MMP activity is regulated in part through secretion as inactive proenzymes and activation by proteolytic processing to smaller molecular weight forms. This regulated activity of MMPs usually requires protease activity as well as autolytic mechanisms. MMPs are inhibited by endogenous tissue inhibitors of matrix metalloproteinases (TIMPs). For the MMP, Gelatinase A (GelA) (MMP-2; 72 kD gelatinase; type IV collagenase; E.C. 3.4.24.24), the specific proteolytic activator is known to be another member of the MMP family, namely MT-MMP. In contrast to other MMPs, MT-MMP is predominantly expressed as an integral membrane protein. There are six known subtypes of MT-MMP, hence the designations MT1-MMP for MMP-14, MT2-MMP for MMP-15, MT3-MMP for MMP-16, MT4-MMP for MMP-17, MT5-MMP for MMP-24 and MT6-MMP for MMP-25. All subtypes of MT-MMP, except for MT4-MMP, effect a cleavage in 72 kD proGelA to initiate a proteolytic "cascade" to 66 kD (intermediate), 59 kD (active) and 43 kD ("mini") forms of GelA. MT-MMP is capable of activating GelA that is complexed with a specific inhibitory protein, TIMP-2. This places MT-MMP expression and/or activity as a major control point in the regulation of ECM turnover.

Trabecular meshwork (TM) is the tissue located at the irido-corneal angle of an eye's anterior segment. The TM is where the aqueous secreted by the ciliary epithelium flows out of the eye. The cells of the TM reside either on collagenous beams, or trabeculae, or embedded in the ECM associated with the canal of Schlemm. The canal of Schlemm is an endothelium-lined channel into which the aqueous drains. The intraocular fluid pressure (IOP) is maintained through a balance of the secretion and outflow of aqueous. Normal IOP is slightly above venous pressure, in part resulting from outflow resistance at the TM. TM outflow resistance is believed to be the result of the hydrodynamic properties of the ECM macromolecules of the TM and the ECM associated with the trabeculae.

For the complex of potentially blinding eye diseases termed primary open angle glaucoma (POAG) the hallmark of which is an insidious, progressive increase in IOP, a prevailing theory of the etiology of the disease is a dysfunction in the regulation of ECM turnover at the level of the TM. There is a biochemical lesion localized to the TM, which manifests as a general excess of ECM or as an imbalance with respect to specific components of the ECM, either of which impairs the ability of fluid to leave the eye at its normal physiological rate. It has been proposed that pharmacological intervention to reduce accumulated ECM could result in a lowering of the elevated IOP characteristic of these diseases.

A therapeutic small organic molecule capable of increasing MT-MMP expression has been decribed by Ito et al. (Ito et al., Eur. J. Biochem. 251, 353–358 (1998)). As described by Ito et al., a trifluoperazine treatment of human cervical fibroblasts resulted in MT1-MMP-induced activation of Gelatinase A (GelA). Trifluoperazine had previously been categorized as a therapeutic "antipsychotic." Ito et al. however, classified trifluoperazine as a calmodulin antagonist, and made a similar claim for another calmodulin inhibitor, W-7, although the effect from the later compound was not particularly pronounced. Ito et al. deduced that calmodulin negatively regulates MT-MMP expression.

Using Western blot immunochemistry, the presence of MT-MMP has been documented in human ocular tissues other than TM cells, as well as in fresh and cultured porcine TM cells. (Alexander, J. and Acott, T. S., Invest. Ophthalmol. Vis. Sci. 40 (ARVO Abstracts): S506, #2670 (1999)). (Smine, A. and Plantner, J. J., Curr. Eye Res. 16:925 (1997)). In neither case was activation of GelA documented, although Alexander and Acott described increased expression of MT1-MMP with phorbol ester (phorbol 12-myristate 13-acetate). Phorbol ester, however, does not have therapeutic usefulness since it is a known carcinogen.

In addition to trifluoperazine and phorbol ester, the following agents have been shown to increase MT-MMP expression and/or GelA activation in cells other than those of the TM.

Concanavalin A
Interleukin-1α
Orthovanadate
A Hexapeptide derived from Elastin
Cytochalasin D
Monensin
Tumor Necrosis Factor-alpha.
Bacterial Lipopolysaccharide
Hydrogen Peroxide
Oxidized Low Density Lipoproteins
Hepatocyte Growth Factor/Scatter Factor
beta-Amyloid Peptide
Activated Protein C
Growth Hormone
Interleukin VIII
Glycyl-L-Histidyl-L-Lysine-$Cu^{2+}$
Lysophosphatidic Acid A search of U.S. patents found only one patent, U.S. Pat. No. 5,260,059, covering agents that increase the activity of matrix metalloproteinases (MMPs). The '059 patent discloses a method of treating glaucoma by providing TM cells with an array of macromolecules, including matrix metalloproteinase-1 (MMP-1), matrix metalloproteinase-2 (MMP-2) and matrix metalloproteinase-3 (MMP-3). The class of MMPs designated as MT-MMPs had not been characterized at the time the '059 patent was filed. At the time of filing the '059 patent, physiologic activation of GelA was suspected of being brought about by means of autocatalytic mechanisms alone. Other molecules specifically mentioned in the '059 patent are basic heparin-binding growth factor, nerve growth factor, interleukin-1, interleukin-6, phorbol ester, calcium ions, zinc ions, plasmin, trypsin, and aminophenyl mercuric acetate (APMA).

Accordingly, a need still exists in the art to provide compositions and methods for the treatment of diseases termed primary open angle glaucoma.

SUMMARY OF THE INVENTION

Small organic molecules in accordance with the present invention are therapeutically useful in the treatment of diseases termed primary open angle glaucoma by having a pharmacological effect on cells and tissue. The subject small organic molecules increase the expression or enzymatic activity of MT-MMP, or a similar enzyme expressed in the TM, that activates GelA. Activation of GelA leads to increased degradation of ECM and a subsequent increase in aqueous outflow with a resultant decrease in IOP.

The small organic molecules of the present invention are also useful in establishing model systems for finding new drug therapies for diseases such as primary open angle glaucoma. To accomplish the same, the subject small organic molecules are used to modulate TM cells and tissues in vitro to effect increased expression and/or activity of MT-MMP. Evidence for this would be the production of active species of GelA from proGelA. The activation of GelA may be demonstrated utilizing proGelA either secreted endogenously by TM cells, or added exogenously as a purified enzyme to experimental tissue or cells. In this respect it is important to note that aqueous humor has abundant proGelA. Enhancement of MT-MMP levels or activity in the cells of the outflow system of the eye would make GelA from proGelA locally available for proteolytic remodelling of ECM.

Given the importance of ECM regulation throughout the tissues and organs of the body, it is not surprising that many diseases have, as part of their pathology, an association with excessive degradation of ECM as a result of increased MMP activity. Drugs to inhibit MMP activity would be useful as therapies for diseases associated with the apparent loss of normal function and regulation of MMP. The present invention therefor includes therapeutic methods of treating particular diseases through cellular regulation of MT-MMP activity and/or expression using the small organic molecules of the present invention.

Accordingly, it is an object of the present invention to provide small organic molecules effective in the treatment of primary open angle glaucoma.

Another object of the present invention is to provide small organic molecules effective in the cellular regulation of MT-MMP activity and/or expression.

Another object of the present invention is to provide a method of effectively treating primary open angle glaucoma.

Another object of the present invention is to provide a method of effectively treating particular diseases through cellular regulation of MT-MMP activity and/or expression.

Another object of the present invention is to provide a method of manufacturing small organic molecules effective in the treatment of particular diseases through cellular regulation of MT-MMP activity and/or expression.

Still another object of the present invention is to provide a method of manufacturing small organic molecules effective in the treatment of primary open angle glaucoma.

These and other objectives and advantages of the present invention, some of which are specifically described and others that are not, will become apparent from the detailed description and claims that follow.

DETAILED DESCRIPTION OF THE INVENTION

The following detailed description is provided to enable any person skilled in the art to which the present invention pertains to make and use the same, and sets forth the best mode contemplated by the inventors of carrying out the subject invention.

The present invention is the use of small organic molecules that have a pharmacological effect on cells and tissues to increase the enzymatic activity and/or expression of one or more membrane-type matrix metalloproteinases (MT-MMPs), or a similar enzyme, expressed in the trabecular meshwork (TM) of an eye to activate Gelatinase A (GelA) for the treatment of primary open angle glaucoma.

The use of the subject small organic molecules of the present invention for increasing cell membrane expression of MT-MMPs, and as a result, for activating GelA, increases the turnover and reduces the accumulation of extracellular matrix. Activating GelA in the TM increases outflow of aqueous and lowers intraocular pressure, thereby having therapeutic potential in the treatment of primary open angle glaucoma.

An additional use of the subject small organic molecules of the present invention is for increasing cell membrane expression of one or more MT-MMPs in the development of in vitro models, which could be used in the discovery of new medical treatments. In general, the small organic molecules of the present invention could contribute to the discovery of new treatments for any ocular disease with a pathophysiology involving changes in expression of one or more MT-MMPs and activation of GelA.

The small organic compounds of the present invention are generally represented by FIG. 1 below:

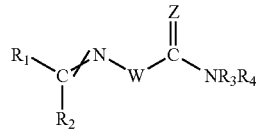

FIG. 1 wherein W is selected from the group consisting of oxygen, sulfur and $C_{1-20}$ hydroxylated carbon group;

Z is selected from the group consisting of oxygen and sulfur;

$R_1$ is branched or unbranched and substituted or unsubstituted selected from the group consisting of $C_{6-25}$ aryl such as for example but not limited to phenyl or naphthyl, $C_{3-20}$ cycloalkyl such as for example but not limited to saturated bicyclic carbocyclic or tricyclic carbocyclic rings, $C_{3-20}$ cycloalkenyl such as for example but not limited to unsaturated bicyclic carbocyclic or tricyclic carbocyclic rings, $C_{3-30}$ heterocyclyl such as for example but not limited to 3-tetrahydrofuranyl, 2-tetrahydrothienyl, 4-piperidinyl, 2-pyrrolidinyl or 3-morpholinyl, $C_{6-30}$ heteroaryl such as for example but not limited to furanyl, imidazolyl, quinolinyl, thiazolyl, indolyl, 3-thienyl, 2-benzofuranyl or 4-pyridyl, $C_{6-30}$ aryloxy such as for example but not limited to phenoxy, $C_{6-30}$ arylalkoxy such as for example but not limited to phenylmethoxy, $C_{6-30}$ aryloxycarbonyl such as for example but not limited to naphthyloxycarbonyl, $C_{6-30}$ arylaminocarbonyl such as for example but not limited to naphthylaminocarbonyl, $C_{6-30}$ arylalkyl such as for example but not limited to phenylmethyl, $C_{6-30}$ aryloyl such as for example but not limited to benzoyl, $C_{6-30}$ arylalkylcarbonyl such as for example but not limited to phenylmethylcarbonyl, $C_{6-30}$ arylalkoxycarbonyl such as for example but not limited to phenylmethoxycarbonyl, $C_{6-30}$ arylthioalkyl such as for example but not limited to phenylthiopropyl, $C_{6-30}$ arylalkenyl such as for example but not limited to phenylpropenyl, $C_{6-30}$ arylalkynyl such as for example but not limited to phenylethynyl, $C_{6-30}$ aryloxyalkyl such as for example but not limited to phenoxymethyl, $C_{6-30}$ arylalkylthioalkyl such as for example but not limited to phenylmeththiomethyl, $C_{6-30}$ arylalkoxyalkyl such as for example but not limited to phenylpropoxyethyl, $C_{6-30}$ arylthiocarbonyl such as for example but not limited to phenylthiocarbonyl, $C_{6-30}$ arylalkylaminocarbonyl such as for example but not limited to naphthylpropylaminocarbonyl, $C_{6-30}$ N-alkyl-N-arylaminocarbonyl such as for example but not limited to N-octyl-N-phenylaminocarbonyl, $C_{6-30}$ N-arylaminosulfonyl such as for example but not limited to naphthylaminosulfonyl, $C_{6-30}$ N-arylaminosulfinyl such as for example but not limited to N-naphthylaminosulfinyl, $C_{6-30}$ arylsulfonyl such as for example but not limited to naphthylsulfonyl, $C_{6-30}$ arylsulfinyl such as for example but not limited to naphthylsulfinyl, $C_{6-30}$ aryloyloxy such as for example benzoyloxy, $C_{6-30}$ arylthio such as for example phenylthio, $C_{6-30}$ arylalkylthio such as for example but not limited to phenylmethylthio, $C_{6-30}$ arylacyloxy, $C_{6-30}$ arylalkylsulfonyl such as for example but not limited to phenylmethylsulfonyl, $C_{6-30}$ arylalkylsulfinyl such as for example but not limited to naphthylpropylsulfinyl, $C_{6-30}$ arylalkylthiocarbonyl such as for example but not limited to naphthylpropylthiocarbonyl, $C_{6-30}$ N-alkyl-N-arylaminosulfonyl such as for example but not limited to N-octyl-N-phenylaminosulfonyl, $C_{6-30}$ N-alkyl-N-arylaminosulfinyl such as for example but not limited to N-butyl-N-phenylaminosulfinyl, $C_{6-30}$ aryloxycarbonylalkylcarbonyl such as for example but not limited to phenoxycarbonylmethylcarbonyl, $C_{6-30}$ aryloylthio such as for example but not limited to naphthoyloylthio and $C_{6-30}$ arylacylthio such as for example but not limited to benzoylthio, and $R_1$ as defined above when substituted is substituted with one or more substituents selected from the group consisting of $C_{1-25}$ alkyl such as for example but not limited to methyl, ethyl or propyl, $C_{1-25}$ alkenyl such as for example but not limited to methenyl, propenyl or octenyl, $C_{1-25}$ alkynyl such as for example but not limited to ethynyl, butynyl or hexynyl, $C_{1-25}$ alkoxy such as for example but not limited to methoxy, propoxy or butoxy, $C_{1-25}$ alkenoxy such as for example but not limited to methenoxy, propenoxy or octenoxy, hydroxy, carboxy, amino, $C_{1-25}$ (N-alkylcarbonyl) amino such as for example but not limited to (N-methylcarbonyl)amino, $C_{1-25}$ (N-alkylcarbonyl)-N-alkylamino such as for example but not limited to (N-methylcarbonyl)-N-propylamino, $C_{1-25}$ (N-alkylcarbonylalkyl)amino such as for example but not limited to (N-methylcarbonylpropyl)amino, cyano, nitro, $C_{6-30}$ arylazo such as for example but not limited to azobenzene, sulfo, sulfino, sulfhydryl, halo such as for example fluoro, chloro, bromo, or iodo, $C_{1-25}$ haloalkyl such as for example but not limited to fluoromethyl or chloropropyl, trifluoromethyl, $C_{1-25}$ trifluoromethylalkyl such as for example trifluoromethylpropyl, $C_{6-30}$ arylalkyl such as for example but not limited to phenylmethyl, $C_{6-30}$ aryl such as for example but not limited to phenyl or naphthyl, $C_{1-25}$ N-alkylamino such as for example but not limited to N-methylamino, $C_{1-25}$ N-dialkylamino such as for example but not limited to N-dimethylamino, $C_{1-25}$ (N-alkyl-N-alkenyl)amino such as for example but not limited to (N-methyl-N-propenyl)amino, $C_{1-25}$ N-dialkenylamino such as for example but not limited to N-dipropenylamino, $C_{1-25}$ alkylsulfonyl such as for example but not limited to propylsulfonyl, $C_{1-25}$ alkylsulfinyl such as for example but not limited to methylsulfinyl, $C_{1-25}$ alkylthio such as for example but not limited to methylthio, hydrido, $C_{1-25}$ cyanoalkyl such as for example but not limited to cyanobutyl, $C_{1-25}$ acyl such as for example but not limited to acetyl, $C_{1-25}$ alkylcarbonyloxy such as for example but not limited to methylcarbonyloxy, nitroso, $C_{1-25}$ alkoxyalkyl such as for example but not limited to methoxypropyl, $C_{1-25}$ alkoxycarbonyl such as for example but not limited to methoxycarbonyl, $C_{1-25}$ hydroxyalkyl such as for example but not limited to hydroxybutyl, thiocarboxy, $C_{1-25}$ thiocarboxyalkyl such as for example but not limited to thiocarboxypropyl, $C_{1-25}$ alkylthiocarbonyl such as for example but not limited to butylthiocarbonyl, $C_{1-25}$ alkylthiocarbonylalkyl such as for example but not limited to methylthiocarbonylethyl, $C_{1-25}$ alkoxythiocarbonyl such as for example but not limited to methoxythiocarbonyl, $C_{1-25}$ alkoxythiocarbonylalkyl such as for example but not limited to methoxythiocarbonylpropyl, sulfamoyl, sulfinamoyl, $C_{1-25}$ N-alkylsulfamoyl such as for example but not limited to N-methylsulfamoyl, $C_{1-25}$ N-dialkylsulfamoyl such as for example but not limited to N-dipropylsulfamoyl, $C_{1-25}$ N-alkylsulfinamoyl such as for example but not limited to N-propylsulfinamoyl, $C_{1-25}$ N-dialkylsulfinamoyl such as for example but not limited to N-dimethylsulfinamoyl, $C_{1-25}$ sulfamoylalkyl such as for example but not limited to sulfamoylmethyl, $C_{1-25}$ sulfinamoylalkyl such as for example but not limited to sulfinamoylpropyl, aminocarbonyl, $C_{1-25}$ aminocarbonylalkyl such as for example but not limited to aminocarbonylmethyl, $C_{1-25}$ N-alkylaminocarbonyl such as for example but not limited to N-propylaminocarbonyl, $C_{1-25}$ N-dialkylaminocarbonyl such as for example but not limited to N-dimethylaminocarbonyl, $C_{1-25}$ alkoxycarbonylamino such as for example but not limited to propoxycarbonylamino, thiocarbamoyl, $C_{1-25}$ thiocarbamoylalkyl such as for example but not limited to thiocarbamoylpropyl, $C_{1-25}$ (N-alkyl)thiocarbamoyl such as for example but not limited to (N-methyl)thiocarbamoyl, $C_{1-25}$ (N-dialkyl)thiocarbamoyl such as for example but not limited to (N-dimethyl)thiocarbamoyl, aminothio, $C_{1-25}$ alkylaminothio such as for example but not limited to propylaminothio, $C_{1-25}$ N-dialkylaminothio such as for example but not limited to N-dimethylaminothio, $C_{1-25}$ cycloalkyl such as for example but not limited to saturated mono-, bi- or tricyclic carbocyclic rings, $C_{1-25}$ cycloalkenyl such as for example but not limited to unsaturated mono-, bi- or tricyclic carbocyclic rings, $C_{1-25}$ aryloxy such as for example but not limited to phenoxy, $C_{1-25}$ cycloalkoxy such as for example but not limited to cyclopentoxy, $C_{1-25}$ cycloalkenoxy such as for example but not limited to cyclopentenoxy, heterocycloxy, $C_{1-25}$ heteroaryloxy, $C_{1-25}$ heteroaryl such as for example but not limited to pyridyl, pyridino, morpholinyl or morpholino, heterocyclic amines, heterocyclic amides such as for example but not limited to piperidino or piperidinosulfamoyl, N- or S-oxo and N- or S-thioxo;

$R_2$ is branched or unbranched and substituted or unsubstituted selected from the group consisting of hydrido, $C_{1-10}$ alkyl such as for example but not limited to methyl, propyl or butyl, $C_{1-10}$ alkenyl such as for example but not limited to methenyl, propenyl or octenyl, $C_{1-10}$ alkynyl such as for example ethynyl, butynyl or heptynyl, cyano, $C_{1-10}$ haloalkyl such as for example but not limited to fluoromethyl, chloropropyl or fluorooctyl, trifluoromethyl, $C_{6-15}$ cycloalkyl such as for example but not limited to cycloheptyl or cyclooctyl, $C_{6-15}$ cycloalkenyl such as for example but not limited to cyclooctenyl or cyclononenyl, $C_{6-15}$ heterocyclyl such as for example but not limited to 2-tetrahydrofuranyl, 3-tetrahydrothienyl, 4-piperidinyl, 2-pyrrolidinyl or 3-morpholinyl, $C_{6-30}$ aryl such as for example but not limited to phenyl or naphthyl, $C_{6-30}$ heteroaryl such as for example but not limited to furanyl, imidazolyl, quinolinyl, thiazolyl, indolyl, 2-thienyl, 3-benzofuranyl or 4-pyridyl, halo, nitro, $C_{6-30}$ alkylaryl such as for example but not limited to methylphenyl or propylphenyl, $C_{6-30}$ alkoxyaryl such as for example but not limited to ethoxyphenyl or butoxynaphthyl, $C_{1-15}$ alkylcarbonyl such as for example but not limited to methylcarbonyl or propylcarbonyl, hydroxycarbonyl, aminocarbonyl, $C_{1-15}$ N-alkylaminocarbonyl such as for example but not limited to N-butylaminocarbonyl or N-propylaminocarbonyl and $C_{1-15}$ alkoxycarbonyl such as for example but not limited to methoxycarbonyl or propoxycarbonyl, and $R_2$ as defined above may be substituted with one or more substituents as defined above for $R_1$;

$R_3$ is branched or unbranched and substituted or unsubstituted selected from the group consisting of hydrido, $C_{1-12}$ alkyl such as for example but not limited to methyl or propyl, $C_{1-12}$ alkenyl such as for example but not limited to ethenyl or butenyl, $C_{1-12}$ alkynyl such as for example but not limited to octynyl or heptynyl, $C_{1-20}$ alkoxyalkyl such as for example but not limited to methoxypropyl or ethoxybutyl, $C_{1-20}$ alkoxyalkenyl such as for example but not limited to methoxypropenyl or ethoxybutenyl, $C_{1-20}$ alkenoxyalkyl such as for example but not limited to methenoxypropyl or ethenoxybutyl and $C_{1-20}$ alkenoxyalkenyl such as for example methenoxymethenyl or ethenoxypropenyl, and $R_3$ as defined above may be substituted with one or more substituents as defined above for $R_1$; and $R_4$ is branched or unbranched and substituted or unsubstituted selected from the group consisting of hydrido, $C_{1-12}$ alkyl such as for example but not limited to methyl or butyl, $C_{1-12}$ alkenyl such as for example but not limited to methenyl or propenyl, $C_{1-12}$ alkynyl such as for example but not limited to methynyl or butynyl, $C_{1-20}$ alkoxyalkyl such as for example but not limited to methoxypropyl, $C_{1-20}$ alkoxyalkenyl such as for example but not limited to methoxypropenyl, $C_{1-20}$ alkenoxyalkyl such as for example methenoxypropyl, $C_{1-20}$ alkenoxyalkenyl such as for example methenoxypropenyl, $C_{6-30}$ aryl such as for example but not limited to phenyl or naphthyl, $C_{6-30}$ cycloalkyl such as for example but not limited to saturated mono-, bi- or tricyclic carbocyclic rings, $C_{6-30}$ cycloalkenyl such as for example but not limited to unsaturated mono-, bi- or tricyclic carbocyclic rings, $C_{6-30}$ heterocyclyl such as for example but not limited to 3-tetrahydrofuranyl, 2-tetrahydrothienyl, 3-piperidinyl, 2-pyrrolidinyl or 3-morpholinyl and $C_{6-30}$ heteroaryl such as for example but not limited to furanyl, imidazolyl, quinolinyl, thiazolyl, indolyl, 3-thienyl, 2-benzofuranyl or 4-pyridyl, and $R_4$ as defined above may be substituted with one or more substituents as defined above for $R_1$.

Most preferably, $R_1$ as defined above is selected from the group consisting of phenyl, benzoyl, 2,6-difluorophenyl, 4-trifluoromethylphenyl, 3,4-dimethoxyphenyl, 4-tert-butylphenyl, 4-methylphenyl, 4-methoxyphenyl, 4-phenoxyphenyl and 2-thienyl.

Most preferably, $R_2$ as defined above is selected from the group consisting of cyano, cyclopentanyl, phenyl and trifluoromethyl.

Most preferably, $R_3$ as defined above is selected from the group consisting of hydrido and alkyl.

Most preferably, $R_4$ as defined above is selected from the group consisting of phenyl, cyclohexyl and alkyl.

Also preferable is $R^3$ and $R^4$ fused in a heterocyclic ring incorporating an amido nitrogen selected from the group consisting of pyrrolidino, piperidino, 4-methylpiperidino and morpholino.

In the case where $R_3$ and $R_4$ are fused in a heterocyclic ring, the same may also include substituents such as for example but not limited to hydrido, alkyl, alkenyl, alkynyl, alkoxyalkyl, alkoxyalkenyl, alkenoxyalkyl or alkenoxyalkenyl as described in detail above. An example not intended to be limiting would be the following glyoxylonitrile, aryl-, O-carbamoyl oxime of FIG. 2 below:

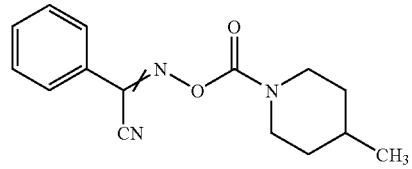

FIG. 2

Additional small organic compounds of the present invention are generally represented by FIG. 3 below:

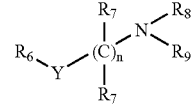

FIG. 3 wherein $R_6$ is branched or unbranched and substituted or unsubstituted selected from the group consisting of $C_{6-25}$ aryl such as for example but not limited to phenyl or naphthyl, $C_{3-20}$ cycloalkyl such as for example but not limited to saturated bicyclic carbocyclic or tricyclic carbocyclic rings, $C_{3-20}$ cycloalkenyl such as for example but not limited to unsaturated bicyclic carbocyclic or tricyclic carbocyclic rings, $C_{3-30}$ heterocyclyl such as for example but not limited to 3-tetrahydrofuranyl, 2-tetrahydrothienyl, 4-piperidinyl, 2-pyrrolidinyl or 3-morpholinyl, $C_{6-30}$ heteroaryl such as for example but not limited to furanyl, imidazolyl, quinolinyl, thiazolyl, indolyl, 3-thienyl, 2-benzofuranyl or 4-pyridyl, $C_{6-30}$ arylalkyl such as for example but not limited to phenylmethyl, $C_{6-30}$ arylthioalkyl such as for example but not limited to phenylthiopropyl, $C_{6-30}$ arylalkenyl such as for example but not limited to phenylpropenyl, $C_{6-30}$ arylalkynyl such as for example but not limited to phenylmethynyl, $C_{6-30}$ aryloxyalkyl such as for example but not limited to phenoxymethyl, $C_{6-30}$ arylalkylthioalkyl such as for example but not limited to phenylmeththiomethyl and $C_{6-30}$ arylalkoxyalkyl such as for example but not limited to phenylpropoxyethyl, and $R_6$ as defined above when substituted is substituted with one or more substituents selected from the group consisting of hydroxy, carboxy, amino, cyano, nitro, nitrate, $C_{1-25}$ alkyl such as for example but not limited to methyl, ethyl or propyl, $C_{1-25}$ alkenyl such as for example but not limited to methenyl, propenyl or octenyl, $C_{1-25}$ alkynyl such as for example but not limited to ethynyl, butynyl or hexynyl, $C_{1-25}$ alkoxy such as for example but not limited to methoxy, propoxy or butoxy, $C_{1-25}$ alkenoxy such as for example but not limited to methenoxy, propenoxy or octenoxy, hydroxy, carboxy, amino, $C_{1-25}$ (N-alkylcarbonyl) amino such as for example but not limited to (N-methylcarbonyl)amino, $C_{1-25}$ (N-alkylcarbonyl)-N-alkylamino such as for example but not limited to (N-methylcarbonyl)-N-propylamino, $C_{1-25}$ (N-alkylcarbonylalkyl)amino such as for example but not limited to (N-methylcarbonylpropyl)amino, $C_{6-30}$ arylazo such as for example but not limited to azobenzene, sulfo, sulfino, sulfhydryl, halo such as for example but not limited to fluoro, chloro, bromo, or iodo, $C_{1-25}$ haloalkyl such as for example but not limited to fluoromethyl or chloropropyl, trifluoromethyl, $C_{1-25}$ trifluoromethylalkyl such as for example trifluoromethylpropyl, $C_{6-30}$ arylalkyl such as for example but not limited to phenylmethyl, $C_{6-30}$ aryl such as for example but not limited to phenyl or naphthyl, $C_{1-25}$ N-alkylamino such as for example but not limited to N-methylamino, $C_{1-25}$ N-dialkylamino such as for example but not limited to N-dimethylamino, $C_{1-25}$ (N-alkyl-N-alkenyl)amino such as for example but not limited to (N-methyl-N-propenyl)amino, $C_{1-25}$ N-dialkenylamino such as for example but not limited to N-dipropenylamino, $C_{1-25}$ alkylsulfonyl such as for example but not limited to propylsulfonyl, $C_{1-25}$ alkylsulfinyl such as for example but not limited to methylsulfinyl, $C_{1-25}$ alkylthio such as for example but not limited to methylthio, hydrido, $C_{1-25}$ cyanoalkyl such as for example but not limited to cyanobutyl, $C_{1-25}$ acyl such as for example but not limited to acetyl, $C_{1-25}$ alkylcarbonyloxy such as for example but not limited to methylcarbonyloxy, nitroso, $C_{1-25}$ alkoxyalkyl such as for example but not limited to methoxypropyl, $C_{1-25}$ alkoxycarbonyl such as for example but not limited to methoxycarbonyl, $C_{1-25}$ hydroxyalkyl such as for example but not limited to hydroxybutyl, thiocarboxy, $C_{1-25}$ thiocarboxyalkyl such as for example but not limited to thiocarboxypropyl, $C_{1-25}$ alkylthiocarbonyl such as for example but not limited to butylthiocarbonyl, $C_{1-25}$ alkylthiocarbonylalkyl such as for example but not limited to methylthiocarbonylethyl, $C_{1-25}$ alkoxythiocarbonyl such as for example but not limited to methoxythiocarbonyl, $C_{1-25}$ alkoxythiocarbonylalkyl such as for example but not limited to methoxythiocarbonylpropyl, sulfamoyl, sulfinamoyl, $C_{1-25}$ N-alkylsulfamoyl such as for example but not limited to N-methylsulfamoyl, $C_{1-25}$ N-dialkylsulfamoyl such as for example but not limited to N-dipropylsulfamoyl, $C_{1-25}$ N-alkylsulfinamoyl such as for example but not limited to N-propylsulfinamoyl, $C_{1-25}$ N-dialkylsulfinamoyl such as for example but not limited to N-dimethylsulfinamoyl, $C_{1-25}$ sulfamoylalkyl such as for example but not limited to sulfamoylmethyl, $C_{1-25}$ sulfinamoylalkyl such as for example but not limited to sulfinamoylpropyl, aminocarbonyl, $C_{1-25}$ aminocarbonylalkyl such as for example but not limited to aminocarbonylmethyl, $C_{1-25}$ N-alkylaminocarbonyl such as for example but not limited to N-propylaminocarbonyl, $C_{1-25}$ N-dialkylaminocarbonyl such as for example but not limited to N-dimethylaminocarbonyl, $C_{1-25}$ alkoxycarbonylamino such as for example but not limited to propoxycarbonylamino, thiocarbamoyl, $C_{1-25}$ thiocarbamoylalkyl such as for example but not limited to thiocarbamoylpropyl, $C_{1-25}$ (N-alkyl)thiocarbamoyl such as for example but not limited to (N-methyl)thiocarbamoyl, $C_{1-25}$ (N-dialkyl)thiocarbamoyl such as for example but not limited to (N-dimethyl)thiocarbamoyl, aminothio, $C_{1-25}$ alkylaminothio such as for example but not limited to propylaminothio, $C_{1-25}$ N-dialkylaminothio such as for example but not limited to N-dimethylaminothio, $C_{1-25}$ cycloalkyl such as for example but not limited to saturated mono-, bi- or tricyclic carbocyclic rings, $C_{1-25}$ cycloalkenyl such as for example but not limited to unsaturated mono-, bi- or tricyclic carbocyclic rings, $C_{1-25}$ aryloxy such as for example but not limited to phenoxy, $C_{1-25}$ cycloalkoxy such as for example but not limited to cyclopentoxy, $C_{1-25}$ cycloalkenoxy such as for example but not limited to cyclopentenoxy, heterocycloxy, $C_{1-25}$ heteroaryloxy, $C_{1-25}$ heteroaryl such as for example but not limited to pyridyl, pyridino, morpholinyl or morpholino, heterocyclic amines, heterocyclic amides such as for example but not limited to piperidino or piperidinosulfamoyl, N- or S-oxo and N- or S-thioxo;

Y is selected from the group consisting of O and S;

the $R_7$ groups may be the same or different selected from the group consisting of H or C1–15 alkyl;

$R_8$ is branched or unbranched and substituted or unsubstituted selected from the group consisting of hydrido, trifluoromethyl, cyano, $C_{1-12}$ alkyl such as for example but not limited to methyl or butyl, $C_{1-12}$ alkenyl such as for example but not limited to methenyl or propenyl, $C_{1-12}$ alkynyl such as for example but not limited to methynyl or butynyl, $C_{1-25}$ alkoxy such as for example but not limited to methoxy, propoxy or butoxy, $C_{1-25}$ alkenoxy such as for example but not limited to methenoxy, propenoxy or octenoxy, $C_{1-25}$ alkynoxy such as for example but not limited to methynoxy, propynoxy or octynoxy, $C_{1-25}$ alkylthio such as for example but not limited to methylthio, propylthio or octylthio, $C_{1-25}$ alkylcarboxy such as for example but not limited to methylcarboxy, propylcarboxy or octylcarboxy, $C_{1-25}$ alkenylcarboxy such as for example but not limited to methenylcarboxy, propenylcarboxy or octenylcarboxy, $C_{1-25}$ alkynylcarboxy such as for example but not limited to methynylcarboxy, propynylcarboxy or octynylcarboxy, $C_{1-25}$ aminoalkyl such as for example but not limited to aminomethyl, aminopropyl or aminooctyl, $C_{1-25}$ alkylaminoalkyl such as for example but not limited to propylaminomethyl, ethylaminopropyl or butylaminooctyl, $C_{1-25}$ dialkylaminoalkyl such as for example but not limited to dipropylaminomethyl, diethylaminopropyl or dibutylaminooctyl, $C_{6-30}$ aryl such as for example but not limited to phenyl or naphthyl, $C_{6-30}$ cycloalkyl such as for example but not limited to saturated mono-, bi- or tricyclic carbocyclic rings, $C_{6-30}$ cycloalkenyl such as for example but not limited to unsaturated mono-, bi- or tricyclic carbocyclic rings, $C_{6-30}$ heterocyclyl such as for example but not limited to 3-tetrahydrofuranyl, 2-tetrahydrothienyl, 3-piperidinyl, 2-pyrrolidinyl or 3-morpholinyl, $C_{6-30}$ heteroaryl such as for example but not limited to furanyl, imidazolyl, quinolinyl, thiazolyl, indolyl, 3-thienyl, 2-benzofuranyl or 4-pyridyl, $C_{6-30}$ arylalkyl such as for example but not limited to phenylmethyl or naphthylpropyl, $C_{6-30}$ cycloalkylalkyl such as for example but not limited to saturated mono-, bi- or tricyclic alkylated carbocyclic rings, $C_{6-30}$ cycloalkenylalkyl such as for example but not limited to unsaturated mono-, bi- or tricyclic alkylated carbocyclic rings, $C_{6-30}$ cycloalkylcarboxy such as for example but not limited to cyclopentylcarboxy, $C_{6-30}$ cycloalkenylcarboxy such as for example but not limited to cyclopentenylcarboxy, $C_{6-30}$ heterocyclyalkyl such as for example but not limited to heterocyclyoctyl, $C_{6-30}$ heteroarylalkyl such as for example but not limited to heterophenylmethyl, $C_{6-30}$ arylcarboxy such as for example but not limited to naphthylcarboxy, $C_{6-30}$ heterocyclylcarboxy, and $C_{6-30}$ heteroarylcarboxy such as for example but not limited to heteronaphthylcarboxy, and $R_8$ as defined above may be substituted with one or more substituents as defined above for $R_6$;

$R_9$ is either

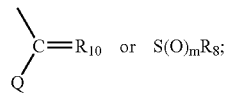

$R_{10}$ is selected from the group consisting of O, S, CH—$NO_2$, N—$NO_2$, N—$S(O)_2$—$CH_3$ and N—CN;

Q is $NR_8R_8$ whereby the $R_8$ groups may be fused in a heterocyclic ring, the same may also include substituents such as for example but not limited to hydrido, $C_{1-12}$ alkyl, $C_{1-12}$ alkenyl, $C_{1-12}$ alkynyl, $C_{1-25}$ alkoxyalkyl, $C_{1-25}$ alkoxyalkenyl, $C_{1-25}$ alkenoxyalkyl or $C_{1-25}$ alkenoxyalkenyl as described in detail above;

m is an integer less than 3; and n is an integer less than 7.

Preferred molecules having the general structure of FIG. 3 above include for example but are not limited to molecules where $R_6$ is naphthyl (alpha- or beta-) or 2,3-dichlorophenyl, Y is oxygen, both $R_7$ groups are hydrido, n is two or three, $R_8$ is isopropyl and $R_9$ is

where $R_{10}$ is oxygen and Q is $NR_8R_8$ with one $R_8$ group hydrido and the other hydrido or methyl. Additionally, certain molecules of the present invention may exist in different isomeric forms. The present invention contemplates all such isomers both individually in pure form, and in admixture, including racemic mixtures.

Additional small organic compounds of the present invention are generally represented by FIG. 4 below:

FIG. 4

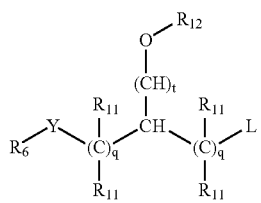

wherein $R_6$ is the same as defined for $R_6$ of FIG. 3 and may be substituted with one or more substituents as defined above for $R_6$;

Y is the same as defined for Y of FIG. 3 above;

$R_{11}$ is selected from the group consisting of hydrido, $C_{1-15}$ branched or straight alkyl and $C_{1-15}$ branched or straight alkenyl;

$R_{12}$ is selected from the group consisting of hydrido and $C_{1-15}$ alkyl;

L is selected from the group consisting of nitrate, $YR_{13}$ and $NR_8R_9$;

$R_{13}$ is selected from the group consisting of $C_{1-15}$ alkyl, $C_{1-15}$ alkenyl, $C_{1-15}$ alkynyl, $C_1l_{15}$ haloalkyl, trifluoromethyl and cyanomethyl;

$R_8$ is the same as defined for $R_8$ of FIG. 3 and may be substituted with one or more substituents as defined above for $R_8$;

$R_9$, $R_{10}$, Q and m are the same as defined for $R_9$, $R_{10}$, Q and m respectively of FIG. 3 above;

q is an integer less than 5; and t is an integer less than 9.

Additional compounds of the present invention based on principles of nonclassical bioisosteres, are illustrated by the general structures of FIGS. 5 through 8 below:

FIG. 5
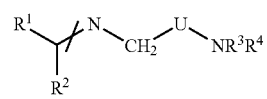

FIG. 6
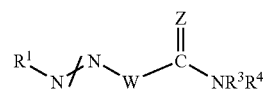

FIG. 7
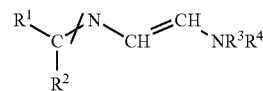

FIG. 8
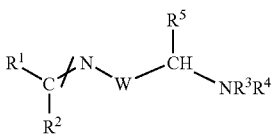

wherein W, Z, $R_1$, $R_2$, $R_3$, and $R_4$ are as defined above in FIG. 1;

U is sulfinyl or sulfonyl; and $R_5$ is selected from the group consisting of hydrido, cyano, halo, trifluoromethyl, haloalkyl, alkyl, alkenyl, alkynyl, aryl, aryloxy, alkoxy, alkenoxy, cycloalkyl, cycloalkenyl, cycloalkoxy, cycloalkenoxy, heterocyclyl, heterocycloxy, heteroaryl and heteroaryloxy, as further defined for substituents of $R_1$ in FIG. 1 above.

Certain small organic compounds of the present invention may exist in different isomeric forms, in particular, isomers related to an oxime nitrogen-carbon bond, which are depicted in FIGS. 1 through 8 by the symbol "⇌". The invention contemplates all such isomers both individually, in pure form and in admixture, including racemic mixtures.

Examples of small organic molecules of the present invention include but are not limited to adenylyl cyclase (AC) inhibitors such as for example but not limited to 9-(tetrahydro-2'-furyl)adenine, 2',5'-dideoxyadenosine and miconazole, phospholipase D (PLD) activators such as but not limited to roxithromycin, fluoride ion, bradykinin, progesterone, endothelin, vasopressin, 4-hydroxynonenal, interleukin-11, angiotensin II, N-(6-aminohexyl)-5-chloro-1-naphthalenesulfonamide and oxidized low density lipoprotein, cyclic adenosine monophosphate (cAMP) phosphodiesterase (CAP) activators such as for example but not limited to phosphatidic acids such as dioleoyl, dioctanoyl and 1-stearoyl-2-arachidonyl-sn-glycerol-3-phosphate, phosphatidic acid analogues such as thiophosphatidic acid and phosphatidic acid (PA) containing alkyl ether, or vinyl ether linkages rather than ester bonds and pyrazinoyl guanidine, protein kinase A inhibitors such as for example but not limited to (N-[2-((p-bromocinnamyl)amino)ethyl]-5-isoquinolinesulfonamide, protein phosphatase inhibitors such as for example but not limited to vanadium salts such as potassium bisperoxo(1,10-phenanthroline)oxovanadate and dipotassium bisperoxo(picolinate)oxovanadate, molybdate oxoanions, tungstate oxoanions and dephostatins such as 3,4-dihydroxy-N-methyl-N-nitrosoaniline and 3,6-dihydroxy-N-methyl-N-nitrosoaniline, phosphatidate phosphohydrolase inhibitors/cationic amphiphiles such as for example but not limited to propranolol, tetracaine, mepacrine, desmethylimipramine, chlopromazine and desipramine, Rho activators such as for example but not limited to sphingosine-1-phosphate, lipid lowering agents or hyperlipoproteinemics such as for example but not limited to 2-tetradecylglycidic acid, 5-(tetradecyloxy)-2-furoic acid, 3-thiadicarboxylic acid, 3-(4-methylpiperazin-1-yl)-1-phenylpropanone, 6,7-dihydro-5H-dibenz[c,e]azepine, N-2-n-butylindazolone, 4-phenyl-5,5-dicarbethoxy-2-pyrrolidinone, 4-(4-hydroxy-3-iodophenoxy)3,5-diiodohydrocinnamic acid, 1-methyl-4-piperidyl bis(ρ-chlorophenoxy)acetate, 2-[[1-methyl-2-[3-(trifluoromethyl)phenyl]ethyl]amino]ethanol benzoate ester and 5-methylpyrazinecarboxylic acid 4-oxide and concanavalin A (Con A) receptor lingands such as for example but not limited to acetylcholinesterase and complement protein 1q.

The small organic molecules of the present invention are described in still greater detail in the examples that follow.

EXAMPLE 1

Small Molecules that Increase Expression or Activity of a Cell-associated Component with Gelatinase Activity, Detected Using a Cell-based Screening Assay that Measures Hydrolysis of a Thiopeptolide Substrate A. Thiopeptolide Assay Used to Detect Cell-Associated Gelatinase Activity Ascribed to MT-MMP:

Rhesus monkey TM cells are cultured and maintained for at least two weeks in 96-well microtiter plates in a growth medium such as Dulbecco's Modified Eagles' Medium (DMEM) plus 15 percent (v/v) fetal bovine serum (FBS) containing 1% bovine calf serum or a medium more suitable for endothelial cells due to its lower serum content such as MCDB 131 supplemented with endothelial cell growth supplement, 1% or less FBS or bovine calf serum and defined supplements as described by Knedler and Ham, In Vitro Cellular and Dev. Biol. 23:481 (1987). Two days before molecule testing, the medium is replace by a defined, serum-free medium such as Minimum Essential Medium (MEM) containing defined supplements as described by Schachtschabel and Binninger, Z.f.Gerontol. 26:243 (1993), but preferably using a basal medium such as MCDB 131 containing defined supplements, because of the absence of interfering substances that could bind or compete with test compounds and because of its ability to maintain endothelial-like cells such as TM cells as a stable, nonproliferative monolayer while optimizing expression of native structural and functional attributes. Unless specifically noted, all molecules tested were prepared as stock solutions in dimethyl sulfoxide (DMSO) with a final concentration of 10 mg/ml. The stocks were stored in a dessicator at −20 degrees Celsius. In testing the molecules, the molecules were diluted to final concentrations of 0.3 ug/ml and 15 ug/ml in a simplified culture medium based on Ames' medium, called Concanavalin A (Con A) conditioning medium (CACM). The monkey TM cells were incubated with the test molecules for 48 hours. Control medium of CACM plus DMSO and a positive control with 5 ug/ml Con A plus DMSO were run in parallel. At the end of the incubation period, the experimental media were replaced with 100 uL of the buffer that is part of the thiopeptolide assay mixture (50 mmol/L HEPES, 5 mmol/L CaCl$_2$, 3.5 mmol/L KCl, 106 mmol/L NaCl, 0.02% (v/v) Brij 35, pH 7.5). Next 100 uL of a doubly (2×) concentrated mixture of the thiopeptolide substrate (from a forty times (40×) concentrated DMSO stock, to give 1 mmol/L final concentration) freshly combined with the thiol reagent (5,5'dithiobis(2-nitrobenzoic acid (DTNB) from a twenty times (20×) concentrated DMSO stock to give 1 mmol/L) were added to each well and were incubated at 37 degrees Celsius for two hours with gentle agitation.

At the end of the incubation period, by means of a spectrophoto-metric plate reader, the optical density (OD) at 410 nm was determined for each well after automatic subtraction of a blank value for a well containing reaction mixture but without cells. The average OD at the two-hour end point for each test molecule at all concentrations in triplicate was calculated. This calculation was interpreted to be a measure of cell-associated MT-MMP level, equivalently defined as either its activity (a catalytic property of the enzyme) or expression (number of functional molecules). The percent difference in OD for each sample compared to the CACM control reflects the effectiveness of each test molecule or combination of molecules in eliciting increases in MT-MMP levels. As an alternate to the end point OD reading, one may use the mean rate of appearance of the reaction product (mean V), calculated from the best linear fit of the data to absorbance vs. time. In so doing, measurements are taken every five minutes with the first and possibly last time points, that do not contribute to a good linear fit, routinely eliminated.

B. Testing of Small Organic Molecules for Associated MT-MMP Activity:

TM cells were exposed to molecules and combinations of molecules by means of simultaneous addition, from separate stocks, to incubation medium.

1. Piperidyl Carbonyl Nitrile Oxime Molecules:

Piperidyl carbonyl nitrile oxime molecules are synthesized as described in U.S. Pat. No. 4,453,974 incorporated herein in its entirety by reference. Results from molecules tested are set forth below in Table 1.

TABLE 1

| Molecule | Conc. umol/L | Percent Activation Over control value |
|---|---|---|
| 1 | 0.9 | 48.1 |
| (MeO, MeO-phenyl C(=N-O-C(=O)-N-piperidyl)CN structure) | 47.31 | 260.4 |
| 2 | 1.0 | 33.8 |
| (2,6-difluorophenyl C(=N-O-C(=O)-N-piperidyl)CN structure) | 51.1.1 | 420.5 |
| 3 | 0.9 | 14.8 |

TABLE 1-continued

| Molecule | Conc. umol/L | Percent Activation Over control value |
|---|---|---|
| 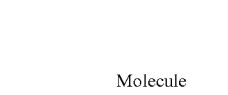 | 42.9.1 | 350.1 |

2. Aryloxydialkylurea Molecules:

Aryloxydialkylurea molecules are synthesized as described in U.S. Pat. No. 5,021,429 incorporated herein in its entirety by reference. Results from molecules tested are set forth below in Table 2.

TABLE 2

| Molecule | Conc. umol/L | Percent Activation Over control value |
|---|---|---|
| 4 | 1.0 | 5.9 |
| | 49.6 | 73.4 |
| 5 | 1.1 | (−16.4) |
| | 57.0 | 94.9 |
| 6 | 1.0 | 2.2 |
| | 52.4 | 207.9 |
| 7 | 1.0 | (−7.9) |
| | 49.2 | 274.0 |

3. Guanabenz Molecules:

Guanabenz molecules are commercially available from Sigma Aldrich Corporation, St. Louis, Mo. Results from molecules tested are set forth below in Table 3.

TABLE 3

| Molecule | Conc. umol/L | Percent Activation Over control value |
|---|---|---|
| 8 | 2.6 | 2.9 |
| | 12.98 | 12.7 |
| | 64.91 | 54.3 |
| | 129.81 | 106.8 |
| 9 | 1.18 | 21.4 |
| | 118.44 | 82.4 |
| 10 | 0.3 | (−0.5) |
| | 76.28 | 75.5 |
| 11 | 1.14 | (−20.9) |
| | 57.22 | 88.1 |
| 12 | 1.05 | 3.2 |
| | 52.53 | 101.6 |

4. Tricyclic Molecules:

Tricyclic molecules are commercially available from Sigma Aldrich Corporation, St. Louis, Mo. Results from molecules tested are set forth below in Table 4.

TABLE 4

| Molecule | Conc. umol/L | Percent Activation Over control value |
|---|---|---|
| 13 | 1.1 | 74.6 |
| | 55.9 | 68.5 |
| 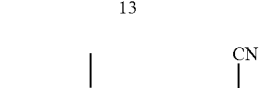 | | |
| 14 | 1.27 | 7.7 |

TABLE 4-continued

| Molecule | Conc. umol/L | Percent Activation Over control value |
|---|---|---|
| 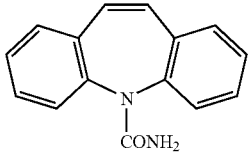 CONH$_2$ | 63.49 | 115.6 |

Regarding negative OD readings in screening assay for MT-MMP, since some color development takes place in the controls, the control OD readings are above zero reflecting a constitutive level of MT-MMP expression. Negative values may likewise result from an artifactual interference in reading the OD at 410 nm, due in part to absorbance properties of the test compound, or from a loss of cells in the well. It is likewise possible that as a result of incubation with a test compound at a particular concentration for 48 hours, there was a net loss of MT-MMP protein molecules or reduced activity of this MMP compared with the control.

As illustrated by the results set forth above, certain structural characteristics are apparently crucial for activity: 1) the piperidine ring; 2) the carbonyl-oxime backbone; 3) the nitrile function; and 4) an aromatic ring attached to the same oxime carbon as the nitrile. Likewise, certain functional groups attached to the aromatic ring increase the activity of the compound.

EXAMPLE 2

Small Molecules that have a Synergistic Effect when Used in Combination, with Each Other or with the Lectin Concanavalin A, on the Increased Expression or Activity of a Cell-associated Component with Gelatinase Activity, Detected Using a Cell-based Screening Assay that Measures Hydrolysis of a Thiopeptolide Substrate Concanavalin A (Con A) binds to mannose groups on cell membrane gycoproteins. Because of its tetravalent nature, Con A binding leads to oligomerization of these "receptors," possibly in the form of heterogeneous aggregates. Con A stimulation elicits increased expression of MT-MMP with concomitant ability to activate proGelA. The response, as measured by the magnitude of zymographic bands and by thiopeptolide assay, is dose-dependent. Thus the effects of co-activation using a submaximal dose of Con A plus treatment with a small molecule that may or may not be active by itself, are measured in the subject activation assay.

A. Co-Activation Assay Used to Detect Cell-associated Gelatinase Activity Ascribed to MT-MMP:

For the coactivation assays, following the preliminary steps set forth above preceding incubation with test compounds in Example 1, cells subsequently undergo one of the following protocols.

Protocol 1. Cells are incubated with a particular test compound for twenty-four hours. This incubation period is followed by a second twenty-four hour incubation period, in which the culture medium containing the first test compound is completely replaced by medium containing 5 ug/ml Con A.

Protocol 2. Cells are incubated with a particular first test compound for twenty-four hours, followed by a second forty-eight hour incubation in which the medium containing the first test compound is completely replaced by medium containing either Con A, as described above, or a second test compound.

Protocol 3. Cells are incubated with a combination of a test compound together with 5 ug/ml Con A for forty-eight hours.

Two controls, with or without 5 ug/ml Con A are run in parallel as described in Example 1. After incubation with these agents, cells are processed in equivalently to those in Example 1. Instead of comparison of the OD values with a CACM control, the results are compared with samples using Con A alone, or with a single test compound as described in Protocol 2 above, as set forth in Table 5 below.

TABLE 5

| Molecule | Protocol | Conc. umol/L (with Con A unless noted otherwise) | Activity (% increase over Con A above, or as otherwise noted) |
|---|---|---|---|
| 6 | 1 | 104.8 | 183.9 |
| 6 | 2 | 34.9 | 49.0 |
| 6 | 2 | 100.0 | 70.9 |
| 7 | 2 | 49.1 | 59.8 |
| 6 and 3 | 2 | 34.9:14.3 | 18.1 (above 3 only) |
| 6 and 3 | 2 | 100.0:42.9 | 39.6 (above 3 only) |
| 13 | 1 | 1.1 | 18.1 |
| 13 | 1 | 55.9 | 109.5 |

A convenient form for administering one or more small organic molecules of the present invention to increase Gelatinase A activity in ocular cells is through a pharmaceutically acceptable composition comprising one or more of the following:

one or more small organic molecules or one or more hydrates of the molecules;

one or more small organic molecules or one or more acid addition salts of the molecules whereby suitable acids include for example but are not limited to mineral acids such as hydrohalic acids, organic acids such as acetic acid, or acids which are sparingly soluble and impart slow-release properties to their salts, such as pamoic acid; and one or more small organic molecules or one or more base addition salts of the molecules whereby suitable salts include those formed from inorganic bases such as hydroxides, carbonates, bicarbonates, or alkoxides of the alkali or alkaline earth metals, organic bases such as mono-, di-, and trialkylamines, alkanolamines, alkene-diamines, phenylalkylamines, cyclic saturated bases, cyclic unsaturated bases or alkylamines forming quaternary salts.

The organic bases forming such salts are of suitable molecular size to be therapeutically acceptable. Acid and base addition salts in accordance with the present invention are prepared by conventional means known by those skilled in the art.

If such pharmaceutically acceptable compositions are formulated as a sterile solution or a suspension in water or other aqueous media, the above formulation would likewise include physiological salt solutions whereby the pH is suitably adjusted and/or buffered and the tonicity is suitably adjusted for optimal absorption, distribution, release, and/or efficacy at the site of action on or within the eye.

If such pharmaceutically acceptable compositions are formulated as a non-aqueous solution or suspension, the above formulation would likewise include an oil, an organic solvent or methyl sulfoxide. Also, formulations of the present invention could likewise include cyclodextrin, a detergent or other non-toxic pharmaceutical excipients combined covalently or noncovalently with a biodegradable or a nonerodable encapsulating substance such as a polymer, as known to those skilled in the art.

The small organic compounds of the present invention are administered to treat glaucoma through a method of delivery to the tissues of the trabecular meshwork of the eye. Methods of such delivery of one or more of the small organic molecules of the present invention include for example but are not limited to application of externally applied eye drops, ointments or implants, injection or insertion a solution, suspension, or sustained-release implant into the anterior chamber or sclera of an eye, external application on the scleral surface of an eye and/or administration as an adjunct pharmaceutical treatment at the time of surgical treatment for glaucoma, as with filtration surgery. Various forms of delivery include single or multiple dosages such that an acute, short term therapy schedule performed once or intermittently over a specified time frame could be useful as an alternative to sustained therapy. In this way, the compounds could be useful for effecting varying degrees of amplification of aqueous outflow through the trabecular meshwork and adjoining structures.

While there is described herein certain specific embodiments of the present invention, it will be manifest to those skilled in the art that various modifications may be made without departing from the spirit and scopeof the underlying inventive concept and that the same is not limited to the particular forms herein described except insofar as indicated by the scope of the appended claims.

We claim:

1. A pharmaceutically acceptable composition useful to increase the activity of Gelatinase A in ocular cells comprising one or more compounds selected from the following formula:

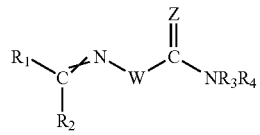

wherein W is selected from the group consisting of oxygen and sulfur;

Z is selected from the group consisting of oxygen and sulfur;

$R_1$ is a substituted or unsubstituted $C_{6-25}$ aryl wherein, when $R_1$ is substituted, $R_1$ is substituted with one or more substituents selected from the group consisting of $C_{1-25}$ alkyl, $C_{1-25}$ alkenyl, $C_{1-25}$ alkynyl, $C_{1-25}$ alkoxy, $C_{1-25}$ alkenoxy, hydroxy, carboxy, amino, $C_{1-25}$ (N-alkylcarbonyl)amino, $C_{1-25}$ (N-alkylcarbonyl)-N-alkylamino, $C_{1-25}$ (N-alkylcarbonylalkyl)amino, cyano, nitro, sulfo, sulfino, sulfhydryl, halo, $C_{1-25}$ haloalkyl, trifluoromethyl, $C_{1-25}$ trifluoromethylalkyl, $C_{6-30}$ arylalkyl, $C_{6-30}$ aryl, $C_{1-25}$ N-alkylamino, $C_{1-25}$ N-dialkylamino, $C_{1-25}$ (N-alkyl-N-alkenyl)amino, $C_{1-25}$ N-dialkenylamino, $C_{1-25}$ alkylsulfonyl, $C_{1-25}$ alkylsulfinyl, $C_{1-25}$ alkylthio, hydrido, $C_{1-25}$ cyanoalkyl, $C_{1-25}$ acyl, $C_{1-25}$ alkylcarbonyloxy, nitroso, $C_{1-25}$ alkoxyalkyl, $C_{1-25}$ alkoxycarbonyl, $C_{1-25}$ hydroxyalkyl, thiocarboxy, $C_{1-25}$ thiocarboxyalkyl, $C_{1-25}$ alkylthiocarbonyl, $C_{1-25}$ alkylthiocarbonylalkyl, $C_{1-25}$ alkoxythiocarbonyl, $C_{1-25}$ alkoxythiocarbonylalkyl, sulfamoyl, sulfinamoyl, $C_{1-25}$ N-alkylsulfamoyl, $C_{1-25}$ N-dialkylsulfamoyl, $C_{1-25}$ N-alkylsulfinamoyl, $C_{1-25}$ N-dialkylsulfinamoyl, $C_{1-25}$ sulfamoylalkyl, $C_{1-25}$ sulfinamoylalkyl, aminocarbonyl, $C_{1-25}$ aminocarbonylalkyl aminocarbonylmethyl, $C_{1-25}$ N-alkylaminocarbonyl, $C_{1-25}$ N-dialkylaminocarbonyl, $C_{1-25}$ alkoxycarbonylamino, thiocarbamoyl, $C_{1-25}$ thiocarbamoylalkyl, $C_{1-25}$ (N-alkyl)thiocarbamoyl, $C_{1-25}$ (N-dialkyl)thiocarbamoyl, aminothio, $C_{1-25}$ alkylaminothio, $C_{1-25}$ N-dialkylaminothio, $C_{1-25}$ cycloalkyl, $C_{1-25}$ cycloalkenyl, $C_{1-25}$ aryloxy, $C_{1-25}$ cycloalkoxy, $C_{1-25}$ cycloalkenoxy, N- or S-oxo and N- or S-thioxo;

$R_2$ is branched or unbranched and substituted or unsubstituted selected from the group consisting of hydrido, $C_{1-10}$ alkyl, cyano, trifluoromethyl, $C_{6-15}$ cycloalkyl or $C_{6-30}$ aryl;

$R_3$ and $R_4$ form a 4 or 5 membered ring with the N, containing no other heteroatom; and a pharmaceutically acceptable aqueous or non-aqueous carrier for delivery on or within the eye.

2. The pharmaceutically acceptable composition of claim 1, wherein $R_1$ is selected from the group consisting of phenyl, benzoyl, 2,6-difluorophenyl, 4-trifluoromethylphenyl, 3,4-dimethoxyphenyl, 4-tert-butylphenyl, 4-methylphenyl, 4-methoxyphenyl and 4-phenoxyphenyl.

3. The composition of claim 1, wherein $R^2$ is selected from the group consisting of cyano, cyclopentanyl, phenyl and trifluoromethyl.

4. The composition of claim 1 wherein $R^3$ and $R^4$ are fused in a heterocyclic ring selected from the group consisting of pyrrolidino, piperidino and 4-methylpiperidino.

5. A pharmaceutically acceptable composition useful to increase the activity of Gelatinase A in ocular cells comprising a compound selected from the group consisting of:

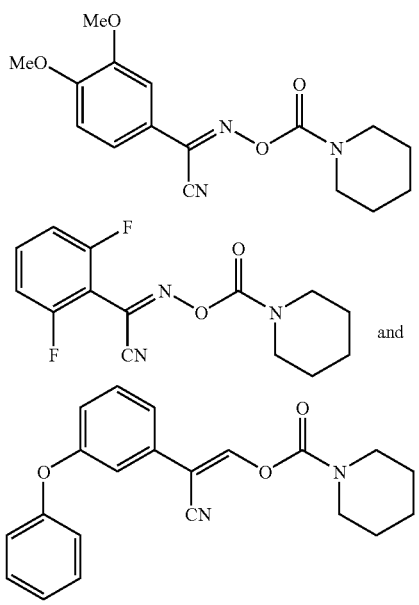

as well as hydrates of the compounds, acid addition salts of the compound, and base addition salts of the compound, and an aqueous or non-aqueous pharmaceutically acceptable carrier for delivery on or within the eye.

6. A pharmaceutically acceptable composition comprising:
one or more compounds selected from the following formula:

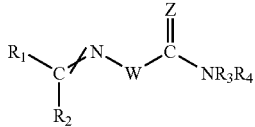

wherein W is selected from the group consisting of oxygen and sulfur;
Z is selected from the group consisting of oxygen and sulfur;
$R_1$ is a substituted or unsubstituted $C_{6-25}$ aryl
wherein, when $R_1$ is substituted, $R_1$ is substituted with one or more substituents selected from the group consisting of $C_{1-25}$ alkyl, $C_{1-25}$ alkenyl, $C_{1-25}$ alkynyl, $C_{1-25}$ alkoxyl, $C_{1-25}$ alkenoxy, hydroxy, carboxy, amino, $C_{1-25}$ (N-alkylcarbonyl)amino, $C_{1-25}$ (N-alkylcarbonyl)-N-alkylamino, $C_{1-25}$ (N-alkylcarbonylalkyl)amino, cyano, nitro, sulfo, sulfino, sulfhydryl, halo, $C_{1-25}$ haloalkyl, trifluoromethyl, $C_{1-25}$ trifluoromethylalkyl, $C_{6-30}$ arylalkyl, $C_{6-30}$ aryl, $C_{1-25}$ N-alkylamino, $C_{1-25}$ N-dialkylamino, $C_{1-25}$ (N-alkyl-N-alkenyl)amino, $C_{1-25}$ N-dialkenylamino, $C_{1-25}$ alkylsulfonyl, $C_{1-25}$ alkylsulfinyl, $C_{1-25}$ alkylthio, hydrido, $C_{1-25}$ cyanoalkyl, $C_{1-25}$ acyl, $C_{1-25}$ alkylcarbonyloxy, nitroso, $C_{1-25}$ alkoxyalkyl, $C_{1-25}$ alkoxycarbonyl, $C_{1-25}$ hydroxyalkyl, thiocarboxy, $C_{1-25}$ thiocarboxyalkyl, $C_{1-25}$ alkylthiocarbonyl, $C_{1-25}$ alkylthiocarbonylalkyl, $C_{1-25}$ alkoxythiocarbonyl, $C_{1-25}$ alkoxythiocarbonylalkyl, sulfamoyl, sulfinamoyl, $C_{1-25}$ N-alkylsulfamoyl, $C_{1-25}$ N-dialkylsulfamoyl, $C_{1-25}$ N-alkylsulfinamoyl, $C_{1-25}$ N-dialkylsulfinamoyl, $C_{1-25}$ sulfamoylalkyl, $C_{1-25}$ sulfinamoylalkyl, aminocarbonyl, $C_{1-25}$ aminocarbonylalkyl aminocarbonylmethyl, $C_{1-25}$ N-alkylaminocarbonyl, $C_{1-25}$ N-dialkylaminocarbonyl, $C_{1-25}$ alkoxycarbonylamino, thiocarbamoyl, $C_{1-25}$ thiocarbamoylalkyl, $C_{1-25}$ (N-alkyl)thiocarbamoyl, $C_{1-25}$ (N-dialkyl)thiocarbamoyl, aminothio, $C_{1-25}$ alkylaminothio, $C_{1-25}$ N-dialkylaminothio, $C_{1-25}$ cycloalkyl, $C_{1-25}$ cycloalkenyl, $C_{1-25}$ aryloxy, $C_{1-25}$ cycloalkoxy, $C_{1-25}$ cycloalkenoxy, N- or S-oxo and N- or S-thioxo;
$R_2$ is branched or unbranched and substituted or unsubstituted selected from the group consisting of hydrido, $C_{1-10}$ alkyl, cyano, trifluoromethyl, $C_{6-15}$ cycloalkyl, $C_{6-30}$ aryl;
$R_3$ and $R_4$ form a 4 or 5 membered ring with the N, containing no other heteroatom;
or one or more hydrates of the one or more compounds in a therapeutically effective amount to increase the activity of Gelatinase A in ocular cells; and
a pharmaceutically acceptable aqueous or non-aqueous carrier for delivery on or within the eye.

7. A pharmaceutically acceptable composition comprising:
one or more compounds selected from the following formula: a compound selected from the following formulation:

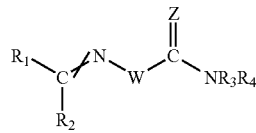

wherein W is selected from the group consisting of oxygen and sulfur;
Z is selected from the group consisting of oxygen and sulfur;
$R_1$ is substituted or unsubstituted $C_{6-25}$ aryl
wherein, when $R_1$ is substituted, $R_1$ is substituted with one or more substituents selected from the group consisting of $C_{1-25}$ alkyl, $C_{1-25}$ alkenyl, $C_{1-25}$ alkynyl, $C_{1-25}$ alkoxy, $C_{1-25}$ alkenoxy, hydroxy, carboxy, amino, $C_{1-25}$ (N-alkylcarbonyl)amino, $C_{1-25}$ (N-alkylcarbonyl)-N-alkylamino, $C_{1-25}$ (N-alkylcarbonylalkyl)amino, cyano, nitro, sulfo, sulfino, sulfhydryl, halo, $C_{1-25}$ haloalkyl, trifluoromethyl, $C_{1-25}$ trifluoromethylalkyl, $C_{6-30}$ arylalkyl, $C_{6-30}$ aryl, $C_{1-25}$ N-alkylamino, $C_{1-25}$ N-dialkylamino, $C_{1-25}$ (N-alkyl-N-alkenyl)amino, $C_{1-25}$ N-dialkenylamino, $C_{1-25}$ alkylsulfonyl, $C_{1-25}$ alkylsulfinyl, $C_{1-25}$ alkylthio, hydrido, $C_{1-25}$ cyanoalkyl, $C_{1-25}$ acyl, $C_{1-25}$ alkylcarbonyloxy, nitroso, $C_{1-25}$ alkoxyalkyl, $C_{1-25}$ alkoxycarbonyl, $C_{1-25}$ hydroxyalkyl, thiocarboxy, $C_{1-25}$ thiocarboxyalkyl, $C_{1-25}$ alkylthiocarbonyl, $C_{1-25}$ alkylthiocarbonylalkyl, $C_{1-25}$ alkoxythiocarbonyl, $C_{1-25}$ alkoxythiocarbonylalkyl, sulfamoyl, sulfinamoyl, $C_{1-25}$ N-alkylsulfamoyl, $C_{1-25}$ N-dialkylsulfamoyl, $C_{1-25}$ N-alkylsulfamoyl, $C_{1-25}$ N-dialkylsulfinamoyl, $C_{1-25}$ sulfamoylalkyl, $C_{1-25}$ sulfinamoylalkyl, aminocarbonyl, $C_{1-25}$ aminocarbonylalkyl aminocarbonylmethyl, $C_{1-25}$ N-alkylaminocarbonyl, $C_{1-25}$ N-dialkylaminocarbonyl, $C_{1-25}$ alkoxycarbonylamino, thiocarbamoyl, $C_{1-25}$ thiocarbamoylalkyl, $C_{1-25}$ (N-alkyl)thiocarbamoyl, $C_{1-25}$ (N-dialkyl)thiocarbamoyl, aminothio, $C_{1-25}$ alkylaminothio, $C_{1-25}$ N-dialkylaminothio, $C_{1-25}$ cycloalkyl, $C_{1-25}$ cycloalkenyl, $C_{1-25}$ aryloxy, $C_{1-25}$ cycloalkoxy, $C_{1-25}$ cycloalkenoxy, N- or S-oxo and N- or S-thioxo;
$R_2$ is branched or unbranched and substituted or unsubstituted selected from the group consisting of hydrido, $C_{1-10}$ alkyl, cyano, trifluoromethyl, $C_{6-15}$ cycloalkyl, $C_{6-30}$ aryl;
wherein $R_3$ and $R_4$ form a 4 or 5 membered ring with the N, containing no other heteroatom;
or one or more acid addition salts of the in a therapeutically effective amount to increase the activity of Gelatinase A in ocular cells and a pharmaceutically acceptable aqueous or non-aqueous carrier for delivery on or within the eye.

8. A pharmaceutically acceptable composition comprising:
one or more compounds defined by the following formula:

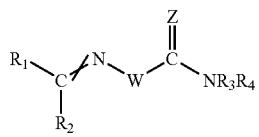

wherein W is selected from the group consisting of oxygen and sulfur;

Z is selected from the group consisting of oxygen and sulfur;

$R_1$ is a substituted or unsubstituted $C_{6-25}$ aryl wherein when $R_1$ is substituted, $R_1$ is substituted with one or more substituents selected from the group consisting of $C_{1-25}$ alkyl, $C_{1-25}$ alkenyl, $C_{1-25}$ alkynyl, $C_{1-25}$ alkoxy, $C_{1-25}$ alkenoxy, hydroxy, carboxy, amino, $C_{1-25}$ (N-alkylcarbonyl)amino, $C_{1-25}$ (N-alkylcarbonyl)-N-alkylamino, $C_{1-25}$ (N-alkylcarbonylalkyl)amino, cyano, nitro, sulfo, sulfino, sulfhydryl, halo, $C_{1-25}$ haloalkyl, trifluoromethyl, $C_{1-25}$ trifluoromethylalkyl, $C_{6-30}$ arylalkyl, $C_{6-30}$ aryl, $C_{1-25}$ N-alkylamino, $C_{1-25}$ N-dialkylamino, $C_{1-25}$ (N-alkyl-N-alkenyl)amino, $C_{1-25}$ N-dialkenylamino, $C_{1-25}$ alkylsulfonyl, $C_{1-25}$ alkylsulfinyl, $C_{1-25}$ alkylthio, hydrido, $C_{1-25}$ cyanoalkyl, $C_{1-25}$ acyl, $C_{1-25}$ alkylcarbonyloxy, nitroso, $C_{1-25}$ alkoxyalkyl, $C_{1-25}$ alkoxycarbonyl, $C_{1-25}$ hydroxyalkyl, thiocarboxy, $C_{1-25}$ thiocarboxyalkyl, $C_{1-25}$ alkylthiocarbonyl, $C_{1-25}$ alkylthiocarbonylalkyl, $C_{1-25}$ alkoxythiocarbonyl, $C_{1-25}$ alkoxythiocarbonylalkyl, sulfamoyl, sulfinamoyl, $C_{1-25}$ N-alkylsulfamoyl, $C_{1-25}$ N-dialkylsulfamoyl, $C_{1-25}$ N-alkylsulfinamoyl, $C_{1-25}$ N-dialkylsulfinamoyl, $C_{1-25}$ sulfamoylalkyl, $C_{1-25}$ sulfinamoylalkyl, aminocarbonyl, $C_{1-25}$ aminocarbonylalkyl aminocarbonylmethyl, $C_{1-25}$ N-alkylaminocarbonyl, $C_{1-25}$ N-dialkylaminocarbonyl, $C_{1-25}$ alkoxycarbonylamino, thiocarbamoyl, $C_{1-25}$ thiocarbamoylalkyl, $C_{1-25}$ (N-alkyl)thiocarbamoyl, $C_{1-25}$ (N-dialkyl)thiocarbamoyl, aminothio, $C_{1-25}$ alkylaminothio, $C_{1-25}$ N-dialkylaminothio, $C_{1-25}$ cycloalkyl, $C_{1-25}$ cycloalkenyl, $C_{1-25}$ aryloxy, $C_{1-25}$ cycloalkoxy, $C_{1-25}$ cycloalkenoxy, N- or S-oxo and N- or S-thioxo;

$R_2$ is branched or unbranched and substituted or unsubstituted selected from the group consisting of hydrido, $C_{1-10}$ alkyl, cyano, trifluoromethyl, $C_{6-15}$ cycloalkyl, $C_{6-30}$ aryl;

$R_3$ and $R_4$ form a 4 or 5 membered ring with the N, containing no other heteroatom;

or one or more base addition salts of the one or more compounds in a therapeutically effective amount to increase the activity of Gelatinase A in ocular cells; and a pharmaceutically acceptable aqueous or non-aqueous carrier for delivery on or within the eye.

9. A method of administering the pharmaceutically acceptable composition of claim 6, 7, or 8 comprising:

formulating said composition as a sterile aqueous or non-aqueous solution; and applying said solution on or within an eye.

10. A method of administering the pharmaceutically acceptable composition of claim 6, 7, or 8 comprising:

providing said composition in the form of an ocular implant; and implanting said ocular implant within an eye.

* * * * *

UNITED STATES PATENT AND TRADEMARK OFFICE
CERTIFICATE OF CORRECTION

PATENT NO. : 7,071,211 B2  Page 1 of 1
APPLICATION NO. : 10/260448
DATED : July 4, 2006
INVENTOR(S) : Bruce Alan Pfeffer et al.

It is certified that error appears in the above-identified patent and that said Letters Patent is hereby corrected as shown below:

In Col. 22, line 58
replace "of the"
with "thereof."

Replace Molecule 8 structure in Table 3

" 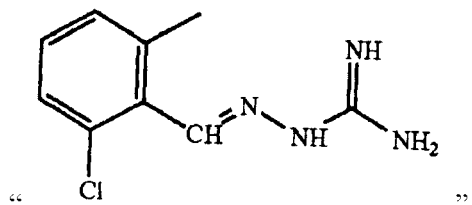 "

with

" 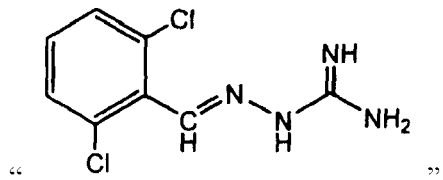 "

Signed and Sealed this

Eighteenth Day of May, 2010

David J. Kappos
*Director of the United States Patent and Trademark Office*